United States Patent [19]

Mandanas et al.

[11] Patent Number: 5,582,816
[45] Date of Patent: Dec. 10, 1996

[54] PREPARATION OF A VISUALLY CLEAR GEL DENTIFRICE

[75] Inventors: Benjamin Y. Mandanas, Freehold; Eric Baines, Branchburg; Prakasarao Mandadi, Hillsborough, all of N.J.

[73] Assignee: Colgate Palmolive Company, New York, N.Y.

[21] Appl. No.: 456,359

[22] Filed: Jun. 1, 1995

[51] Int. Cl.$^6$ ........................................ A61K 7/16
[52] U.S. Cl. ............................... 424/49; 424/57
[58] Field of Search ........................... 424/49–58

[56] References Cited

U.S. PATENT DOCUMENTS

| | | | |
|---|---|---|---|
| 3,538,230 | 11/1970 | Pader et al. | 424/50 |
| 3,689,637 | 9/1972 | Pader | 424/52 |
| 3,906,090 | 9/1975 | Colodney | 424/52 |
| 3,939,262 | 2/1976 | Kim | 424/52 |
| 4,108,978 | 8/1978 | Mazzanobile et al. | 424/49 |
| 4,627,977 | 12/1986 | Gaffar et al. | 424/52 |
| 4,877,602 | 10/1989 | Uematsu et al. | 424/49 |
| 4,894,220 | 1/1990 | Nabi et al. | 424/52 |
| 5,192,529 | 3/1993 | Garlik et al. | 424/47 |
| 5,252,313 | 10/1993 | Collins et al. | 424/49 |
| 5,354,550 | 10/1994 | Collins et al. | 424/49 |
| 5,415,810 | 5/1995 | Lee et al. | 252/545 |
| 5,480,633 | 1/1996 | Simion et al. | 424/70.1 |
| 5,496,540 | 3/1996 | Gaffar et al. | 424/49 |

FOREIGN PATENT DOCUMENTS

| | | | |
|---|---|---|---|
| 2200551 | 6/1991 | United Kingdom | A61K 7/16 |

*Primary Examiner*—Shep K. Rose
*Attorney, Agent, or Firm*—Robert L. Stone; Paul Shapiro

[57] ABSTRACT

Preparation of a visually clear gel dentifrice comprising a precipitated silica polishing agent having a refractive index of about 1.44, a water-swellable synthetic anionic polycarboxylate polymer which is added in solid form and a liquid vehicle comprising water and sorbitol wherein (a) when the total water content is above 30% to about 33% by weight of said dentifrice, sorbitol on a neat basis is present in amount of above 30% to about 36% by weight of said dentifrice (b) when the total water content is about 27% up to below 30% by weight of said dentifrice, sorbitol on a neat basis is present in amount of about 20% up to below 30% by weight of said dentifrice and other humectant if present, is in neat amount of up to 15% by weight of said dentifrice and also adding to said liquid vehicle about 1–4% by weight of dentifrice of solid water-swellable synthetic anionic polycarboxylate polymer.

19 Claims, No Drawings

PREPARATION OF A VISUALLY CLEAR GEL DENTIFRICE

This invention relates to preparation of an antiplaque gel dentifrice which are visually clear.

Dentifrices which are visually clear are appealing to consumers. Numerous visually clear products have been sold commercially as gel dentifrices.

Occasionally, as described in U.S. Pat. No. 3,906,090 to Colodney, it is possible to attain very high clarity and transparency in a gel dentifrice. Frequently, however, because of the need to appropriately balance amounts and types of dentifrices components for optimum effectiveness and for cosmetic considerations other than translucency, clarity is sacrificed and the gel dentifrice, while still clear, is translucent, hazy or cloudy and not transparent. Indeed, the gel dentifrice may be opacified and not clear at all.

The prior art considerations for attaining clarity ranging from haze or translucency to high transparency have, in general, been based upon employing a dentifrice polishing agent having a refractive index of about 1.41 to about 1.47, properly balanced with water (refractive index 1.333) and humectant, most usually glycerine (refractive index 1.473) and sorbitol (refractive index 1.457, as 70% aqueous solution). Since the refractive index of grades of siliceous polishing agents, the most frequently used type of polishing agents in gel dentifrices, is usually about 1.41 to about 1.47, although water ranges in the dentifrices such as up to about 30% by weight have been disclosed, the amount of water is generally kept low, say about 3% by weight, when transparency and not merely turbid translucency is desired.

An exception permitting more water to be used in transparent gel dentifrices is described in U.S. Pat. No. 4,877,602 to Uematsu et al, wherein a special grade of sodium carboxymethyl cellulose binding agent having a viscosity of 5–20 cps measures as 1% aqueous solution at 25° C. is indicated to provide transparency to gel dentifrices wherein the liquid vehicle components vary over a wide range.

In more recent years, water-swellable synthetic anionic polymeric polycarboxylates have been introduced into oral compositions, particularly as agents which improve effectiveness in combating negative conditions such as tartar and plaque. In antiplaque dentifrices, there is desirably present a substantially water insoluble noncationic antibacterial agent such as triclosan (2',4,6'-trichloro-2-hydroxy-diphenyl ether). Such polycarboxylates are disclosed in British Patent Publications 2235133A, 2227660A and 2200551A, each to Colgate Palmolive Company and U.S. Pat. No. 4,894,220 to Nabi et al, the disclosures of each of which are incorporated herein by reference. These disclosures set forth guides to preparing visually clear antiplaque dentifrices wherein there are described gel dentifrices containing a siliceous polishing agent; broad weight ranges of water and humectant are indicated. This general guidance and specific illustrative examples within their parameters can guide the artisan toward some visual translucency but not high transparency.

In antitartar dentifrices such as in U.S. Pat. No. 4,627,977 to Gaffar et al the disclosure of which is incorporated herein by reference, and in antiplaque dentifrices such as those of incorporated aforementioned British Patent Publications 2235133A; 2227660A; 2200551A and U.S. Pat. No. 4,894,220, the polymeric materials have been described as present in a range of amounts such as up to about 3% or 4% by weight.

In practice, it has been observed that high visual clarity has been difficult to attain when the amount of polymer is at least about 1% by weight, and particularly when it is present in amount of about 2% by weight or more. Indeed, even liquid vehicles disclosed in U.S. Pat. No. 4,877,602 have not been employed in conjunction with water-swellable polymers which markedly affect the liquid vehicle.

Such high visual clarity was achieved for gel dentifrice containing about 1% to 2% by weight or more water-swellable synthetic anionic polycarboxylates and a polishing agent having a refractive index of about 1.41 to 1.47 in U.S. Pat. No. 5,252,313 and its Continuation U.S. Pat. No. 5,354,550 with use of particular levels of liquid vehicle, that is about 25–30% by weight water and about 30–45% by weight of neat humectant with at least about 30% by weight of neat sorbitol being present.

It is an advantage of this invention that excellent visual clarity is attained in a dentifrice containing water-swellable synthetic anionic polymer introduced in dry form in mount of about 1–4% with a particular liquid vehicle when the polishing agent present is a precipitated silica having a refractive index of about 1.44, that is 1.435 to 1.444. The liquid vehicle in accordance with this invention includes a sorbitol-water combination different from that of U.S. Pat. Nos. 5,252,313 and 5,354,550 for providing gel dentifrice with superior visual clarity.

Other advantages of the invention will be apparent from consideration of the following specification.

In accordance with certain of its aspects, this invention relates to a method of preparing a visually clear gel dentifrice comprising adding to a liquid vehicle about 5–50% by weight of a dentally acceptable dentifrice precipitated silica polishing agent having a refractive index of about 1.44, and about 0.1–10% by weight of a gelling agent to provide a gel consistency to said dentifrice, said liquid vehicle comprising water and sorbitol wherein (a) when the total water content is above 30% to about 33% by weight of said dentifrice, sorbitol on a neat basis is present in amount of above 30% to about 36% by weight of said dentifrice and (b) when the total water content is about 27% up to below 30% by weight of said dentifrice, sorbitol on a neat basis is present in amount of about 20% up to below 30% by weight of said dentifrice and other humectant if present, is in neat amount of up to 15% by weight of said dentifrice and also adding to said liquid vehicle about 1–4% by weight of dentifrice of solid water-swellable synthetic anionic polycarboxylate polymer.

The dentally acceptable dentifrice precipitated silica polishing agent has a refractive index of about 1.44, that is 1,435 to 1.444. Such precipate silica is currently available from J. M. Huber Corporation under the trademark as Zeodent®. It is noteworthy, that visually clear gels are not satisfactorily obtained when the liquid phase of the gel dentifrice is in accordance with the present invention but the precipated silica polishing agent is a Zeodent® silica which has a refractive index of 1.45.

The polishing agent is present in amount of about 5–50% by weight, preferably about 10–30% and most preferably about 15–25%.

Water has a refractive index of 1.333. Since this is substantially lower than the refractive index of the polishing agent, low amounts of water, for instance about 3% by weight, usually have been employed when high visual clarity is desired. However, since the water swellable synthetic anionic polymeric polycarboxylate is swelled and hydrated by water and moreover when the polymer is present in mount of at least 1% by weight, substantial amounts of water have been used in such formulations. Indeed, in such formulations, 35% of water has been employed to hydrate about 1–2% by weight of solid polymer.

In the present invention it has been found that in a gel dentifrice containing about 5–30% by weight of precipitated silica polishing agent having a refractive index of about 1.44, a particular balance of liquid vehicle components, specifically water and sorbitol even though outside of the parameters of U.S. Pat. No. 5,252,313 and 5,354,550, permits the polymer to be satisfactorily hydrated while still providing a refractive index of the liquid vehicle such that the gel dentifrice is highly transparent.

The liquid vehicle of the dentifrice comprises about 30% to about 33% by weight of total water and about 30% to about 36% by weight of neat sorbitol or about 27% up to below 30% by weight of total water and about 20% up to below 30% by weight of neat sorbitol. Sorbitol is the main or only humectant component. It is commercially available in 70% aqueous solution (refractive index 1.457) and is employed in mount such that as the 70% aqueous solution it is present in amount by weight corresponding to about 31 to below about 42.7%, corresponding to about 22% to less than 30% by weight of neat sorbitol. When the total water content is above 30% to about 33% by weight, preferably about 32% to about 33%, about 30% to about 36% by weight, preferably about 33.5% to about 36% of neat sorbitol is present. When the total water content is about 27% up to below 30% by weight, preferably about 29% to 29.8%, about 20% to about 36% by weight, preferably about 20% to about 24% by weight of neat sorbitol is present. Other humectants can be absent or, if present, be in amount of up to 15% by weight on a neat basis preferably about 3–15%. These include glycerine (typically available in about 99% to about 99.7% aqueous solution), propylene glycol, polypropylene glycol and polyethylene glycol. Glycerine (refractive index 1.473) is preferred. It is preferred not to use polyethylene glycol when substantially water-insoluble noncationic antibacterial agent, such as triclosan, is present.

Water-swellable synthetic anionic polymeric polycarboxylate having a molecular weight of about 1,000 to about 1,000,000, preferably about 30,000 to about 500,000, have been used in optimizing anticalculus effectiveness of linear molecularly dehydrated polyphosphate salts, as disclosed in incorporated U.S. Pat. No. 4,627,977 to Gaffar et al.

The water-swellable synthetic anionic polymeric polycarboxylates are preferably employed as partially or completely neutralized water-swellable alkali metal (or ammonium) salt but may also be used as their free acids. They are incorporated into the liquid vehicle as solids, that is, in dry form, for instance as powders. Preferably they are 4:1 to 1:4 copolymers of maleic anhydride or maleic acid with another polymerizable ethylenically unsaturated monomer, which is very preferably methyl vinyl ether, and the copolymer will have a molecular weight in the range of about 5,000–2,000,000, preferably about 30,000–1,500,000, more preferably about 50,000–1,100,000 and most preferably about 50,000–100,000, as determined by vapor pressure osmometry. A preferred range of molecular weights, by gel permeation chromatography against a polyethylene glycol standard, is about 500,000–1,500,000, more preferably about 1,000,000–1,100,000, e.g., about 1,090,000. GAF's Gantrez® solid grades AN 169, AN 139, AN 119 and S-97, pharmaceutical grade, are useful. The Gantrez polycarboxylates have been reported by their manufacturer to be of molecular weights of about 750,000, 500,000, 250,000 and 70,000, respectively, but by gel permeation chromatography determinations (against a polyethylene glycol standard) the S-97, pharmaceutical grade, is of a molecular weight in the range of about 1,000,000–1,100,000 (the lower molecular weight of 70,000 was determined by vapor pressure osmometry). The polymers such as the Gantrez polymers are incorporated into the gel dentifrices in solid form. The mentioned Gantrezes are all linear copolymers. However, cross-linked polymers, such as those sold under the trademark Carbopol, of B.F. Goodrich, e.g., Carbopols 934, 940 and 941, may be substituted, at least in part (e.g., about 1% or more).

Other water-swellable polymeric polycarboxylates include the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylic acid with methyl or hydroxyethyl methacrylate, methyl or ethyl acrylate, isobutyl vinyl ether or N-vinyl-2-pyrrolidone.

Additional water-swellable polymeric polycarboxylates include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable, also, generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and arthydrides. Other different olefinic monomers copolymerizable with such carboxylic monomers include vinylacetate, vinyl chloride, dimethyl maleate and the like. Copolymers contain sufficient carboxylic salt groups for water-solubility.

The synthetic anionic polymeric polycarboxylate component is mainly a hydrocarbon with optional halogen and O-containing substituents and linkages as present in, for example, ester, ether and OH groups and when present is employed in the instant compositions in approximate weight amounts of 1–4% by weight on a neat basis or polycarboxylate, preferably about 2–3%, more preferably about 2–2.5%.

When, as in the present invention, the water-swellable synthetic anionic polymeric polycarboxylate is used in amount of at least 1% by weight, it is very desirable to employ a substantially water-insoluble noncationic antibacterial agent as described in previously mentioned in incorporated British Patent Publications 2235133A, 2227660A, and 2200551A; and U.S. Pat. No. 4,894,220, for antiplaque effectiveness. These include halogenated diphenyl ethers such as triclosan and 2,2'-dihydroxy-5-5'-dibromo-diphenyl ether as well as phenolic compounds including phenol and its homomogs, mono-and poly-alkyl and aromatic halophenols, resorcinol and its derivatives and bisphenolic compounds. Hexyl resorcinol is particularly worthy of mention. Other types include halogenated salicylanilides, benzoic esters and halogenated carbanilides. When present, the antibacterial agent is employed in an effective antiplaque amount, typically about 0.01–5% by weight, preferably about 0.3–0.5%.

Optionally linear molecularly dehydrated polyphosphate salt anticalculus agent may also or alternatively be present in amount of about 0.1–7% by weight, preferably about 2–5%. These include wholly or partially neutralized water soluble alkali metal (e.g. potassium or preferably sodium) or ammonium salts such as sodium hexamethaphosphate, sodium tripolyphsophate, disodium diacid pyrophosphate, trisodium monoacid pyrophosphate, tetrasodium pyrophosphate and tetrapotassium pyrophosphates as well as mixtures. When both substantially water-insoluble noncationic antibacterial agent and polyphosphate salt are present it is desirable that the weight ratio of polymeric polycarboxylate to polyphosphate be at least about 1.6:1 to about 2.7:1.

Gel dentifrices have their gel consistency provided by a natural or synthetic binder, thickener or gelling agent in proportions of about 0.1 to about 10% by weight, preferably about 0.5 to about 5%.

Suitable thickeners include Irish moss, iota carrageenan, gum tragacanth starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Sodium carboxymethyl cellulose is preferred, even including grades having a viscosity above 20 cps measured as 1% aqueous solution at 25° C., e.g. CMC-7MF and CMC-7MFX available from Hercules.

It will be understood that, as is conventional, the gel dentifrice preparations are to be sold or otherwise distributed in suitably labeled collapsible tubes, typically aluminum, lined lead or opaque or clear plastic, or other squeeze, pump or pressurized dispenser for metering out the contents, having a label describing it in substance, as a gel dentifrice or toothpaste.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxypropane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. the use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("exthoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the gel dentifrices of this invention such as preservatives, silicones, other anticalculus agents, water-soluble dyes, iridescent particles and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, d-tryptophan, dihydrochalcones, sodium cyclamate, perillartine, APM (aspartyl phenyl alanine, methyl ester), saccharine and the like. Suitably, flavor and sweetening agents may together comprise from about 0.1% to 5% or more of the preparation.

The gel dentifrices may be prepared by blending solid materials with liquids to obtain gel consistency with uniform appearance or with stripes. The polycarboxylate is blended in solid, that is dry, form such as a powder. The gel dentifrices typically have a pH of about 4.5 to 9, generally about 5.5 to 8, preferably about 6 to 8.

The following examples are further illustrative of the nature of the present invention, but it is understood that the invention is not limited thereto. All amounts and proportions referred to herein and in the appended claims are by weight unless otherwise indicated.

EXAMPLE 1

The following gel dentifrice is prepared by dispersing Viscarin in glycerine and adding Gantrez S-97 to the dispersion, followed by addition with mixing of sorbitol solution, polyethylene glycol, deionized water and color solution and then of sodium fluoride, sodium saccharin and tetrasodium pyrophosphate. The composition is then heated to 60° C. at which time sodium hydroxide solution is added and heating is stopped. The composition is mixed for 10 additional minutes and transferred as a gel to a Ross mixer in which Zeodent is added to the gel and mixed for about 20 minutes under full vacuum. Finally sodium lauryl sulfate and flavor are added with mixing for 10 minutes under full vacuum.

| | Parts | | |
|---|---|---|---|
| Glycerine (99.5% Solution) | 14.925 | Glyerin | 0.075 Water |
| Sorbitol (70% Solution) | 22.195 | Sorbitol | 9.512 Water |
| Polyethylene Glycol 600 | 3.000 | | |
| Viscarin (Irish Moss) | 0.850 | | |
| Sodium Fluoride | 0.243 | | |
| Sodium Saccharin | 0.300 | | |
| Polyvinylmethyl Ether/Maleic Anhydride-Gantrez S-97 | 1.500 | | |
| Sodium Hydroxide (50% Solution) | 0.500 | Sodium Hydroxide | 0.500 Water |
| Tetrasodium Pyrophosphate | 2.000 | | |
| Precipitated Silica- Zeodent-Refractive Index 1.440 | 23.000 | | |
| Sodium Lauryl Sulfate | 1.200 | | |
| Flavor | 0.950 | | |
| Color Solution (FD&C Blue - 1%) | 0.002 | Color | 0.148 Water |
| Water-deionized | | | 19.000 |
| Total Water | | | 29.235 Parts |

The gel dentifrice is and remains very transparent.

The calculated refractive index of the liquid vehicle components, water, glycerine polyethylene glycol 600, and 70% sorbitol is 1.4271. The gel dentifrice has high visual clarity. A substantial part of water hydrates the swellable Gantrez copolymer. When Zeodent silica of refractive index 1.450 replaces the Zeodent silica of refractive index 1.440, the gel dentifrice is cloudy.

EXAMPLE 2

The following highly clear gel dentifrice is prepared in accordance with the procedure set forth in Example 1 for blending liquids with solids.

|  | Parts | | |
| --- | --- | --- | --- |
| Sorbitol (70%) | 34.095 | Sorbitol | 14.612 Water |
| Polyethylene Glycol 600 | 3.000 | | |
| Viscarin (Irish Moss) | 0.850 | | |
| Sodium Fluoride | 0.243 | | |
| Sodium Saccharin | 0.300 | | |
| Polyvinylmethyl Ether Maleic Anhydride-Gantrez S-97 | 1.500 | | |
| Sodium Hydroxide (50%) | 0.500 | Sodium Hydroxide | 0.500 Water |
| Tetrasodium Pyrophosphate | 2.000 | | |
| Precipitated Silica-Zeodent 113 | 23.000 | | |
| Sodium Lauryl Sulfate | 1.200 | | |
| Flavor | 0.950 | | |
| Color Solution (FD&C Blue-1%) | 0.002 | | 0.148 |
| Water-deionized | | | 17.000 |
| Total Water | | | 32.260 Parts |

In variants of the above examples highly clear gel dentifrices are prepared including triclosan and propylene glycol.

This invention has been described with respect to certain preferred embodiments and it will be understood that modifications and variations thereof obvious to those skilled in the art are to be included within the purview of this application and the scope of the appended claims.

We claim:

1. A method of preparing a visually clear gel dentifrice comprising adding to a liquid vehicle about 5–50% by weight of a dentally acceptable dentifrice precipitated silica polishing agent having a refractive index of about 1.44, about 0.1–10% by weight of a gelling agent to provide a gel consistency to said dentifrice, said liquid vehicle comprising water and sorbitol wherein (a) when the total water content is above 30% to about 33% by weight of said dentifrice, sorbitol on a neat basis is present in amount of above 30% to about 36% by weight of said dentifrice and (b) when the total water content is about 27% up to below 30% by weight of said dentifrice, sorbitol on a neat basis is present in amount of about 20% up to below 30% by weight of said dentifrice and other humectant if present, is in neat amount of up to 15% by weight of said dentifrice and also adding to said liquid vehicle about 1–4% by weight of dentifrice of solid water-swellable synthetic anionic polycarboxylate polymer.

2. The visually clear gel dentifrice claimed in claim 1 wherein said precipitated silica has a refractive index of 1.435 to 1.444.

3. The visually clear dentifrice claimed in claim 1 wherein said polishing agent is present in amount of about 10–30% by weight.

4. The visually clear gel dentifrice claimed in claim 2 wherein said precipitated silica polishing agent is present in amount of about 15–25% by weight.

5. The visually clear gel dentifrice claimed in claim 3 wherein the total water contents above 30% to about 36%.

6. The visually clear gel dentifrice claimed in claim 4 wherein the total water content is about 32% to about 33% and sorbitol on a neat basis is present in amount of about 33.5% to about 36%.

7. The visually clear gel dentifrice claimed in claim 3 wherein the total water content is about 27% up to below 30% by weight and sorbitol on a neat basis is present in amount of 20% to about 24% by weight.

8. The visually clear gel dentifrice claimed in claim 7 wherein the total water content is about 29% to about 29.8% and sorbitol on a neat basis is present in amount of about 20% to about 24% by weight.

9. The visually clear gel dentifrice claimed in claim 1 wherein said liquid vehicle comprises up to about 15% by weight of an additional humectant material.

10. The visually clear gel dentifrice claimed in claim 9 wherein said additional humectant material comprises about 3–15% by weight of at least one of glycerine, propylene glycol, polypropylene glycol and polyethylene glycol.

11. The visually clear gel dentifrice claimed in claim 10 wherein said additional humectant material comprises glycerine.

12. The visually clear gel dentifrice claimed in claim 1 wherein about 0.1–7% by weight of a linear molecularly dehydrated polyphsophate salt anticalculus agent is also present.

13. The visually clear gel dentifrice claimed in claim 12 wherein said polyphsophate salt is present in amount of about 2–5% by weight and is tetrasodium pyrophosphate.

14. The visually clear gel dentifrice claimed in claim 13 wherein said liquid vehicle comprises up to about 15% by weight of an additional liquid humectant material which is at least one of glycerine, propylene glycol, polypropylene glycol and polyethylene glycol.

15. The visually clear gel dentifrice claimed in claim 14 wherein said additional humectant material comprises about 3–10% by weight of at least one of glycerine and polyethylene glycol.

16. The visually clear gel dentifrice claimed in claim 1 wherein an effective antiplaque amount of a substantially water-insoluble non-cationic antibacterial agent is present.

17. The visually clear gel dentifrice claimed in claim 16 wherein said antibacterial agent is triclosan.

18. The visually clear gel dentifrice claimed in claim 1 wherein said polycarboxylate polymer is present in amount of about 2–3% by weight.

19. The visually clear gel dentifrice claimed in claim 18 wherein said polycarboxylate polymer is polyvinyl methyl ether/maleic anhydride copolymer.

* * * * *

UNITED STATES PATENT AND TRADEMARK OFFICE
CERTIFICATE OF CORRECTION

PATENT NO. : 5,582,816
DATED : December 10, 1996
INVENTOR(S) : Benjamin Y. Mandanas, et. al.

It is certified that error appears in the above-indentified patent and that said Letters Patent is hereby corrected as shown below:

Column 2, line 29, cancel "method of preparing a".
Column 2, line 30, cancel "adding to" and insert --in--.
Column 7, line 41, cancel "method of preparing a".
Column 7, line 42, cancel "adding to" and insert --in--.

Signed and Sealed this

Twenty-third Day of September, 1997

*Attest:*

BRUCE LEHMAN

*Attesting Officer*      *Commissioner of Patents and Trademarks*